Figure 1:
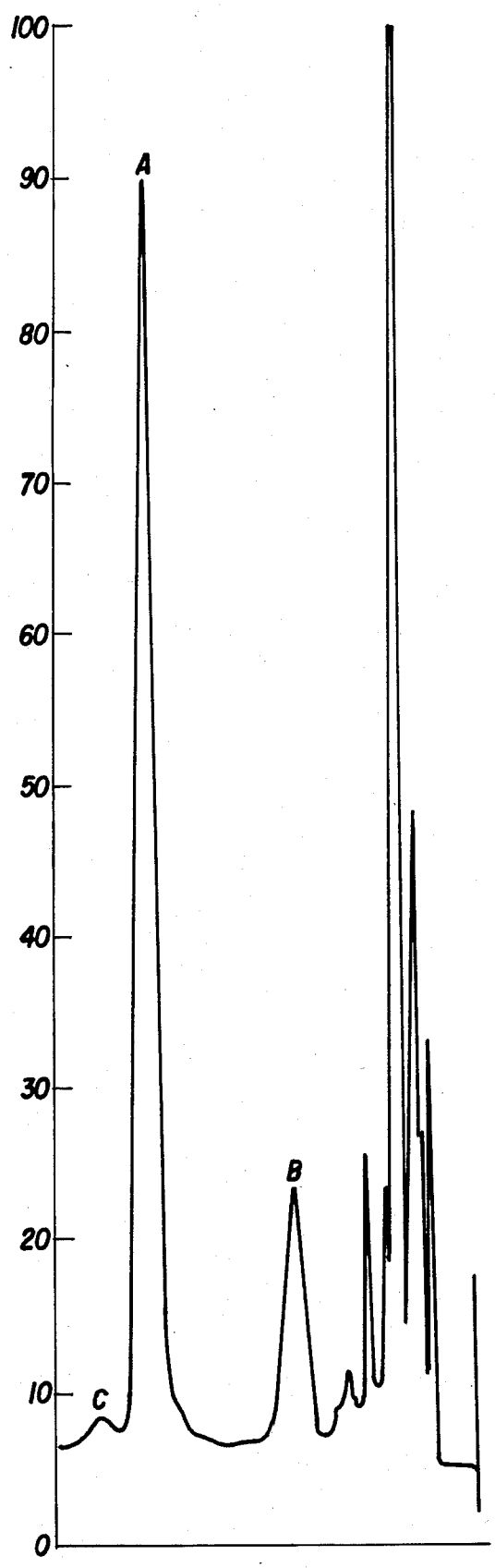

United States Patent [19]

Carobbi et al.

[11] Patent Number: 4,555,271
[45] Date of Patent: Nov. 26, 1985

[54] PROCESS FOR PURIFYING LACTULOSE SYRUP

[75] Inventors: Renato Carobbi, Pistoia; Sandro Miletti, Florence; Vittorio Franci, San Pietro a Sieve, all of Italy

[73] Assignee: Sirac SpA, Milan, Italy

[21] Appl. No.: 621,542

[22] Filed: Jun. 18, 1984

[30] Foreign Application Priority Data

Jun. 20, 1983 [IT] Italy ................ 21689 A/83

[51] Int. Cl.⁴ .............................. C13D 3/14
[52] U.S. Cl. ................... 127/46.2; 127/61
[58] Field of Search .......... 127/30, 46.1, 46.2, 127/55, 61, 62; 536/127

[56] References Cited

U.S. PATENT DOCUMENTS

| 3,505,309 | 4/1970 | Carubelli | 127/46.1 |
| 3,546,206 | 12/1970 | Guth et al. | 127/46.1 |
| 3,716,408 | 2/1973 | Nagasawa et al. | 127/46.1 |
| 3,816,174 | 6/1974 | Nagasawa et al. | 127/46.1 |
| 4,394,178 | 7/1983 | Chao et al. | 127/55 |

FOREIGN PATENT DOCUMENTS

| 47-39545 | 7/1972 | Japan | 127/46.2 |
| 1232554 | 5/1971 | United Kingdom | 127/30 |

Primary Examiner—Ivars Cintins
Attorney, Agent, or Firm—Stevens, Davis, Miller & Mosher

[57] ABSTRACT

A process for purifying commercial lactulose in the form of syrup, comprising a first stage of chemical oxidation with bromine or electrochemical oxidation in the presence of sodium bromide, followed by treating the obtained aqueous solution with ion exchange resins in the following order:
- strong cationic resins of H+ form
- weak anionic resin of OH− form
- strong anionic resin of bisulphite form
- strong cationic resin of H+ form
- weak anionic resin of OH− form.

3 Claims, 3 Drawing Figures

PROCESS FOR PURIFYING LACTULOSE SYRUP

The lactulose syrup sold commercially is generally not pure, and usually contains appreciable quantities of other substances such as lactose, galactose, epilactose etc.

Lactulose or 4-0-$\beta$-D-galactopyranosyl-D-fructose is known to be a synthetic disaccharide currently used in the form of syrup in the treatment of intestinal affections or in the form of crystalline product as a sweetener for replacing saccharose.

There is therefore the requirement of providing the consumer or patient with an improved product from the qualitative aspect by reducing the quantity of contained impurities to the greatest possible extent, even though such impurities are known innocuous mono or disaccharides.

The object of the present invention is to provide a pure lactulose syrup starting from the commercial syrup, of which the average composition is as follows:

| Lactulose | 50% by weight |
| Galactose | 4–8% by weight |
| Lactose | 4–8% by weight |
| Other carbohydrates | 5–10% by weight |

After treatment according to the present invention, the purified syrup composition is on average as follows:

| Lactulose | 50% by weight |
| Lactose | 0.2% by weight |
| Galactose | 0.1% by weight |
| Other carbohydrates | 2% by weight |

Of particular importance is the fact that starting from this purified syrup it is possible to obtain lactulose in the crystalline state not only at very high purity but also with exceptionally high industrial yields exceeding 90%.

The literature describes various processes for reducing the extraneous carbohydrate content of lactulose syrup by using special resins or by the controlled oxidation of the syrup, followed by removal of the aldonic acids formed from the galactose and lactose over normal ion exchange resins.

In the first case, the lactulose is separated from the other carbohydrates by selective absorption on resins, followed by fractional elution. However, these processes have not yet found practical industrial application mainly because of their complexity, time and cost.

In the second case, the purification is accomplished by oxidising the syrup under controlled conditions such as to obtain the conversion of the contained aldoses to aldonic acids, while leaving the lactulose and generally the ketoses unaltered.

These acids are then removed by passage over ion exchange resins.

A process of this type is described in U.S. Pat. No. 3,272,705, according to which the oxidation of the aldoses is accomplished by bromine chemically or electrochemically in the presence of calcium carbonate. Indeed, under these conditions the syrup becomes freed of lactulose by passage over the resins, but a high pressure liquid chromatography analysis carried out under the experimental conditions which are stated further on shows extraneous peaks with a low retention time.

It has now been surprisingly found that if the solution is passed successively through a column of anionic resin in bisulphite form at a temperature of 5° C., and then through a further pair of columns containing strong cationic resin and weak anionic resin, the aforesaid extraneous peaks are considerably reduced.

The present invention therefore provides a process for purifying commercial lactulose syrup, which comprises a first stage in which the product is subjected to chemical oxidation with bromine or alternatively electrochemical oxidation, ie anodic oxidation, in the presence of sodium bromide, followed by treating the oxidised solution with ion exchange resins by means of five successive passages over the following resins:

1: strong cationic resin in H$^+$ form
2: weak anionic resin in OH$^-$ form
3: strong anionic resin in bisulphite form
4: strong cationic resin in H$^+$ form
5: weak anionic resin in OH$^-$ form The passage over the anionic resin in bisulphite form is effected at a temperature of between 0° and 10° C., and preferably 5° C.

The aqueous solution obtained contains lactulose of high purity, with very small concentrations of lactose, galactose and other carbohydrates.

A syrup containing 50% of lactulose by weight and of the aforesaid composition can be obtained by concentration under vacuum.

Chromatographic analysis shows the substantial reduction in the content of extraneous substances or their complete removal, compared with the results obtained for crude lactulose solutions as such or lactulose purified by known methods.

Solution analysis carried out by high pressure liquid chromatography under the following conditions:

Column: $\phi$4 mm; 1=250 mm
Filling: Lichrosorb NH$_2$ (10 microns)
Column temperature: 40±0.5° C.
Detector: UV spectrophotometer-reading at 192 nm
Mobile phase: 20% of a 0.01M aqueous monobasic potassium phosphate solution and 80% of acetonitrile
Flow: 2.5 ml/minute
Quantity injected: 20 $\mu$l of a solution having an approximate concentration of 10% carbohydrates, gives the diagrams of FIGS. 1, 2 and 3, which relate respectively to solutions of crude lactulose, lactulose purified by known methods, ie oxidised with bromine and passed over strong cationic resin in H$^+$ form and over weak anionic resin in OH$^-$ form, and lactulose purified according to the invention. A, B and C indicate the lactulose, galactose and lactose peaks respectively.

Figure 3:
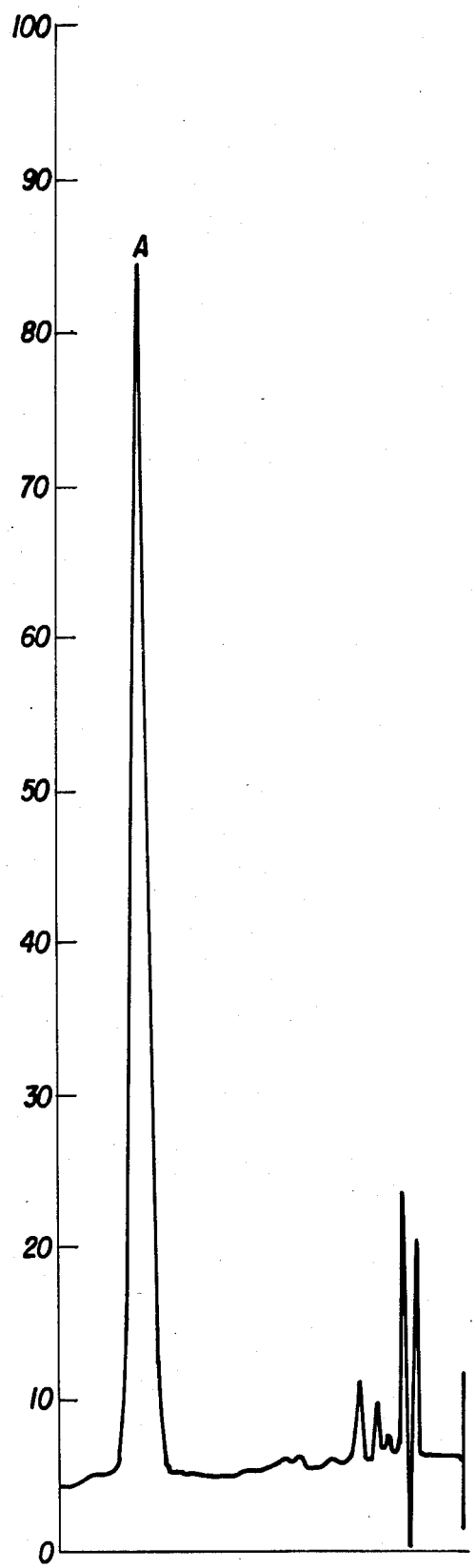

It can easily be seen from FIG. 3 that the peaks corresponding to lactose and galactose are eliminated, and the peaks of other extraneous substances of short retention times are considerably reduced.

Figure 2:
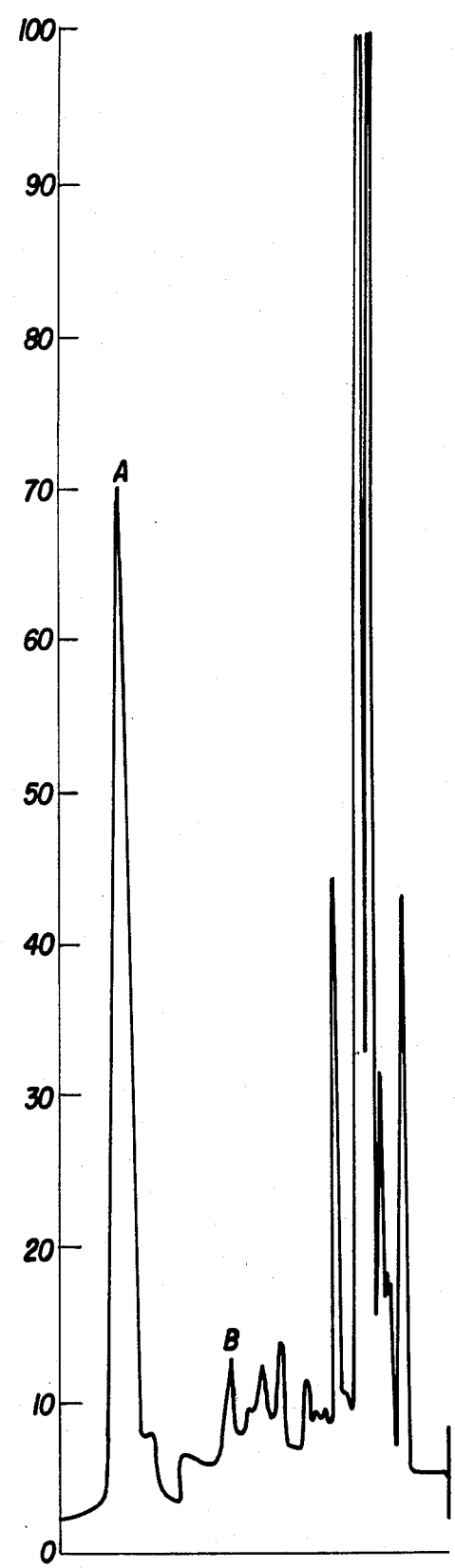

As can be seen from FIG. 2, the product purified by known conventional methods shows much less effective purification.

Lactulose syrup at a weight concentration of about 50%, containing 0.2% of lactose, 0.1% of galactose and less than 2% of other carbohydrates, is well suited to the preparation of high purity crystalline lactulose at high yield with respect to the initial lactulose. The crystalline product can be prepared by concentrating the syrup under vacuum until of solid or pasty consistency, then extracting the mass with ethanol. The amount of alcohol used is very limited, and a large proportion (about 80%) can be recovered, the crystalline product obtained being of high purity (exceeding 98%), and the yield with respect to the initial lactulose can reach 94%.

The following examples are given purely to illustrate the invention.

EXAMPLE 1

500 kg of commercial 50% lactulose syrup containing 4-8% of lactose, 4-8% of galactose and 5-10% of other carbohydrates, 1300 liters of deionised water and 34 kg of calcium carbonate are fed into an enamelled 2000 liter reactor fitted with a stirrer.

Maintaining a temperature of 20° C., 28.4 kg of bromine are added over a period of 2 hours while stirring, and stirring is continued for a further 4 hours until the bromine totally disappears.

The solution is filtered and passed through a column of strong cationic resin in H form (Amberlite IR 120) and through a column of weak anionic resin in OH form (Amberlite IRA 93), and then, after cooling to +5° C., through a column of anionic resin in bisulphite form (Amberlite IRA 400). Finally, the solution is again passed through a column of strong cationic resin in H+ form, and through a column of weak anionic resin in OH− form, and then concentrated under vacuum.

400-450 kg of syrup are obtained containing 50% by weight of lactulose, 0.2% of lactose and 0.1% of galactose, together with other carbohydrates to a total not exceeding 2%. Yield 80-90% with respect to the commercial syrup used.

EXAMPLE 2

200 g of commercial 50% lactulose syrup, 500 ml of deionised water and 2 g of sodium bromide are fed into an electrolytic cell comprising graphite electrodes. A 10% solution of sodium chloride is placed in the cathode space, which is separated from the anode space by a teflon membrane.

A voltage of 8 V is fed across the electrodes, this corresponding to a current of 1 A under the experimental conditions used, and anodic oxidation is continued for 8 hours, continuously adding an aqueous solution of sodium bicarbonate to the anode compartment so as to maintain the pH at 6.

When oxidation is terminated, the mixture is passed through resins as in Example 1.

160-180 g of purified syrup are obtained containing 50% of lactulose of the same degree of purity as Example 1, equivalent to a yield of 80-90%.

It should be noted that the use of sodium bicarbonate in aqueous solution instead of calcium carbonate enables oxidation to proceed regularly without any calcareous incrustations forming on the membrane which separates the anode compartment from the cathode compartment.

EXAMPLE 3

500 kg of pure syrup as obtained in Examples 1 and 2 are fed into a 500 liter enamelled reactor, and are concentrated under a vacuum of 10 Torr, initially under stirring, to a residual water content of 3-4%, after which 200 liters of 96% ethanol are added, and the mixture heated under reflux for 3 hours.

It is filtered at 60° C., the crystalline precipitate washed with alcohol, and dried.

225-237 kg of lactulose crystals are obtained with a purity not less than 98%, equal to a yield of 90-95% with respect to the lactulose contained in the syrup used.

We claim:

1. A process for purifying commercial lactulose syrup, to obtain a syrup with a content of 50% by weight of lactulose, and to reduce the content of lactose, galactose and other carbohydrates to a level not exceeding, respectively, 0.2%, 0.1% and 2% by weight, comprising: oxidizing said commercial lactulose either chemically with bromine or in an electrochemical cell in the presence of sodium bromide to obtain an aqueous solution; successively passing the aqueous solution obtained over the following ion-exchange resins:
    (a) strong cationic resin in H+ form
    (b) weak anionic resin in OH− form
    (c) strong anionic resin in bisulphite form
    (d) strong cationic resin in H+ form
    (e) weak anionic resin in OH− form,
the passage (c) being effected at a temperature of between 0° and 10° C.; and then concentrating the solution under vacuum to a concentration of lactulose of 50% by weight.

2. A process as claimed in claim 1, wherein the passage (c) is effected at 5° C.

3. A process for obtaining lactulose in crystalline form at a purity not less than 98%, consisting of concentrating under vacuum the lactulose syrup purified by the process as claimed in claim 1, to a residual water content of 3 to 4% by weight and extracting the solid mass obtained with ethanol.

* * * * *